(12) United States Patent
Lewandowski et al.

(10) Patent No.: US 7,342,047 B2
(45) Date of Patent: *Mar. 11, 2008

(54) CROSSLINKABLE HYDROPHILIC MATERIALS FROM REACTIVE OLIGOMERS HAVING PENDENT UNSATURATED GROUPS

(75) Inventors: Kevin M. Lewandowski, Inver Grove Heights, MN (US); Duane D. Fansler, Dresser, WI (US); Michael S. Wendland, North St. Paul, MN (US); Steven M. Heilmann, Afton, MN (US); Babu N. Gaddam, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 291 days.

This patent is subject to a terminal disclaimer.

(21) Appl. No.: 10/792,238

(22) Filed: Mar. 2, 2004

(65) Prior Publication Data
US 2005/0194559 A1   Sep. 8, 2005

(51) Int. Cl.
*A61K 47/00* (2006.01)
(52) U.S. Cl. ............... 514/772.1; 514/772.3; 514/772.4; 514/772.6; 424/400
(58) Field of Classification Search ........... 526/82, 526/194; 525/530; 604/304
See application file for complete search history.

(56) References Cited

U.S. PATENT DOCUMENTS

| | | |
|---|---|---|
| RE24,906 E | 12/1960 | Ulrich |
| 3,121,021 A | 2/1964 | Copeland |
| 3,389,827 A | 6/1968 | Abere et al. |
| 4,094,842 A | 6/1978 | Wenzel et al. |
| 4,112,213 A | 9/1978 | Waldman |
| 4,123,423 A | 10/1978 | Wenzel et al. |
| 4,190,566 A | 2/1980 | Noll et al. |
| 4,385,164 A | 5/1983 | Sinclair et al. |
| 4,394,493 A * | 7/1983 | Bartkovitz et al. ......... 525/530 |
| 4,499,896 A | 2/1985 | Heinecke |
| 4,598,004 A | 7/1986 | Heinecke |
| 4,680,352 A | 7/1987 | Janowicz et al. |
| 4,694,054 A | 9/1987 | Janowicz |
| 4,849,458 A | 7/1989 | Reed et al. |
| 5,362,826 A | 11/1994 | Berge et al. |
| 5,506,279 A | 4/1996 | Babu et al. |
| 5,531,855 A | 7/1996 | Heinecke et al. |
| 5,614,310 A | 3/1997 | Delgado et al. |
| 5,653,699 A | 8/1997 | Reed et al. |
| 5,733,570 A | 3/1998 | Chen et al. |
| 5,738,642 A | 4/1998 | Heinecke et al. |
| 5,741,543 A | 4/1998 | Winslow et al. |
| 5,773,534 A | 6/1998 | Antonelli et al. |
| 5,849,325 A | 12/1998 | Heinecke |
| 5,902,836 A | 5/1999 | Bennett et al. |
| 6,007,833 A * | 12/1999 | Chudzik et al. ............ 424/425 |
| 6,171,985 B1 | 1/2001 | Joseph et al. |
| 6,198,016 B1 | 3/2001 | Lucast et al. |
| 6,221,303 B1 | 4/2001 | Steinmann |
| 6,242,423 B1 | 6/2001 | Bardat et al. |
| 6,361,768 B1 | 3/2002 | Galleguillos et al. |
| 6,420,622 B1 | 7/2002 | Johnston et al. |
| 6,448,301 B1 | 9/2002 | Gaddam et al. |
| 6,559,223 B2 | 5/2003 | Green et al. |
| 6,566,575 B1 | 5/2003 | Stickels et al. |
| 6,635,690 B2 | 10/2003 | Heilmann et al. |
| 6,664,306 B2 | 12/2003 | Gaddam et al. |
| 2001/0051178 A1 | 12/2001 | Blatchford et al. |
| 2003/0096908 A1 | 5/2003 | Heilmann et al. |
| 2003/0203011 A1 | 10/2003 | Abuelyaman et al. |
| 2003/0212210 A1 | 11/2003 | Heilmann et al. |
| 2003/0216519 A1 | 11/2003 | Heilmann et al. |
| 2004/0063027 A1 | 4/2004 | Barr et al. |
| 2005/0070688 A1 | 3/2005 | Lewandowski et al. |
| 2005/0131148 A1 | 6/2005 | Lewandowski et al. |
| 2006/0165762 A1 | 7/2006 | Plaut et al. |
| 2006/0292209 A1 | 12/2006 | Lewandowski et al. |

FOREIGN PATENT DOCUMENTS

| | | |
|---|---|---|
| WO | WO 99/13865 | 3/1999 |
| WO | WO 99/13866 | 3/1999 |
| WO | WO 00/42958 | 7/2000 |
| WO | WO 01/60296 A1 | 8/2001 |
| WO | WO 03/086493 A1 | 10/2003 |
| WO | WO 2005/035607 A1 | 4/2005 |

OTHER PUBLICATIONS

Odian, George "Principles of Polymerization" 1991, 19-24.*
Nguyen et al., "Photopolymerizable hydrogels for tissue engineering applications" Biomaterials 23 (2002) 4307-4314.*
Scott et al., "Highly crosslinked, PEG-containing copolymers for sustained solute delivery" Biomaterials 29 (1999) 1371-1380.*
U.S. Appl. No. 10/790,902, filed Mar. 1, 2004, entitled "Crosslinkable Hydrophilic Materials From Reactive Oligomers Having Pendent Photoinitiator Groups".
G. Odian, "Principles of Polymerization", (1991), p. 108, 3rd Edition, John Wiley & Sons, New York.
G. P. Gladyshev and K. M. Gibov, "Polymerization at Advanced Degrees of Conversion", (1970), Keter Press, Jerusalem.
T. Greene and P. G. M. Wuts, (1999), 3rd Edition, Wiley Interscience, New York, N. Y.
ASTM D1003-00.

(Continued)

*Primary Examiner*—Michael P. Woodward
*Assistant Examiner*—Eric E. Silverman
(74) *Attorney, Agent, or Firm*—Kent S. Kokko

(57) ABSTRACT

The present invention provides cross linkable compositions useful in the preparation of hydrophilic gels, and are prepared from obligers having pendent hydrophilic ploy(alkenylene oxide) groups, and pendent pulverizable functional groups, and cross linked by polyfunctional ploy(alkenylene oxides).

31 Claims, No Drawings

OTHER PUBLICATIONS

U.S. Appl. No. 10/672,580, filed Sep. 26, 2003, entitled "Reactive Hydrophilic Oligomers", Lewandowski et al.

U.S. Appl. No. 10/732,715, filed Dec. 10, 2003, entitled "Reactive Hydrophilic Oligomers", Lewandowski et al.

* cited by examiner

CROSSLINKABLE HYDROPHILIC MATERIALS FROM REACTIVE OLIGOMERS HAVING PENDENT UNSATURATED GROUPS

TECHNICAL FIELD OF THE INVENTION

This invention relates to novel hydrophilic, cross linkable oligomer compositions and articles prepared therefrom. The compositions can be useful in preparing gel materials and medical articles incorporating such materials, particularly medical articles useful as wound dressings.

BACKGROUND OF THE INVENTION

Historically, exudate from a wound has been treated by absorbing it using a dressing containing an absorbent material. Such dressings have contained a padded absorbent material attached to an adhesive tape backing. The padded absorbent material is applied to the wound to absorb the wound exudate. A difficulty with this type of dressing is that the scab typically forms in and as part of the pad as the wound heals. Thus, when the dressing is removed, the scab is removed. This problem has been addressed by providing a porous film between the absorbent material and the wound to reduce the likelihood that a scab formed will become attached to the absorbent material.

Some current wound care products use a hydrocolloid absorbent. Such materials typically have poor transparency so the treatment state cannot be observed from the outside. Also, such a material can partially lose its integrity after absorbing wound fluid. Flexibility of hydrocolloid dressings can be poor, which makes it difficult to apply the dressing to a bend portion of a body, such as a joint, etc. The portion of the absorbent in contact with the wound is converted to a gel-like material, and, when the dressing is removed, a portion of this absorbent material can be left in the wound, and must be removed to permit examination and/or before applying another dressing.

More recently the use of so-called "occlusive" dressings for pressure sores and ulcers has gained acceptance. Most of these products are formed from several layers, including at least an inner skin-contacting layer and an outer backing layer. The dressing is applied as a cover for the sore or ulcer in a size providing a margin around the wound area that adhesively seals to the skin. An inner layer contains water-absorptive materials, so that fluid from the wound is absorbed into the layer, making it possible to keep the dressing in place for at least several days. Such occlusive dressings tend to promote healing by maintaining the wound under moist conditions without forming a crust, and serving as a barrier against bacterial infection. Such dressings for "moist wound healing" are particularly useful for dermal burns, traumatic skin deficiencies, incised wounds, and the like.

SUMMARY OF THE INVENTION

Though there are known hydrophilic gel materials useful in medical applications such as wound dressings, many do not have the appropriate balance of absorption and cohesive strength. Thus, additional such materials are needed. Further, it can be desirable to provide an occlusive material that is also transparent and/or flexible for use in a medical article such as a wound dressing or wound packing material. Yet further, it can be desirable to provide compositions that are melt-processible, and contain low residuals content.

The current invention describes reactive, melt-processible materials that may be cast on a web and cured by a chain-growth mechanism to yield uniform coatings, particularly gel coatings. The obligers, crosslinking agent and extent of reaction, or crosslink density, can be varied in order to provide specific properties for a range of applications. The molecular weight of these materials is such that they can easily be processed, giving economic and/or environmental advantages. The materials can be subsequently cured through application of actinic energy, such as UV radiation, to yield improved final mechanical properties. Thus, these materials represent a significant advance of the current art.

Briefly, the present invention provides novel hydrophilic, oligomeric compositions prepared from a first component oligomer containing pendent hydrophilic ploy(alkenylene oxide) groups, pendent pulverizable functional groups, optionally pendent photoinitiator groups and a co-reactive second component crosslinking agent having terminal pulverizable functional groups and a hydrophilic ploy(alkenylene oxide) segment. In embodiments where the first component oligomer does not contain pendent photoinitiator groups, the composition may further comprise a third component photoinitiator, which may be a polymeric photoinitiator.

In one aspect this invention provides a hydrophilic, cross linkable, oligomeric composition comprising:
  a) a first component oligomer comprising a plurality of polymerized monomer units having pendent hydrophilic ploy(alkenylene oxide) groups, and pendent free-radically pulverizable unsaturated groups; and
  b) a hydrophilic ploy(alkenylene oxide) crosslinking agent having pulverizable, ethylenically unsaturated terminal groups.

This invention can have one or more of several advantages. The invention provides a UV cross linkable composition that produces no or minimal by-products, and that achieves its crosslink density by chain-growth addition. The composition is low in viscosity, readily melt processible and coatable, and has minimal residuals content such as solvents, monomers, plasticizers, by-products of condensation reactions or displacement reactions and/or viscosity modifiers. The compositions can rapidly and reliably prepared without requiring specialized equipment and without generating concerns about potentially toxic or irritating unreacted low molecular weight monomeric species.

In another aspect this invention provides a process for making a substrate bearing a coating of a cross linked composition (such as a hydrophilic gel) on at least one surface thereof, comprising the steps of:
  a) coating the cross linkable, oligomeric composition of the invention onto a substrate, and
  b) subjecting said coated cross linkable composition to sufficient actinic energy, in the presence of a photoinitiator, to crosslink said composition.

For performance, environmental, and economic considerations, photoinitiated polymerization is a particularly desirable method for preparing a coating, such as a gel layer directly on the substrate. With this polymerization technique, it is advantageous to create a composition having coatable viscosity of 10,000 centipoise or less (when measured at or below 100° C.), coat the composition on the substrate, then crosslink the components to build strength.

As used herein, the term "melt processible" or simply "processible" is used to refer to oligomeric compositions that possess or achieve a suitable low viscosity for coating or extrusion at temperatures less than the decomposition temperature(s) of the obligers and crosslinking agent and less than the temperature at which premature gelation occurs, using conventional extrusion equipment without the need for addition of residuals such as solvents, monomers, plasticizers and/or viscosity modifiers and without the need for extraordinary pressures. Preferably the composition is melt processable at temperatures less than or equal to 100° C.

In one embodiment, this invention provides absorbent medical articles and hydrophilic, polymeric gel materials for use therein, which are preferably transparent. By "gel" (or "polymer gel" or "polymeric gel material" or "hydrophilic gel") it is meant a gel material capable of swelling on contact with water-based fluids (such as body fluids including blood, plasma, and intracellular fluid or fluids similar to body fluids such as physiological saline), but does not dissolve in water. The gels are substantially continuous, i.e., lacking a cellular or void structure (although minor defects such as entrapped air bubbles or fractures may be present) and thus generally in a solid or semi-solid form. The term "gel" is used regardless of the state of hydration. Preferably, the gel does not include water until it comes in contact with a surface from which it absorbs water (e.g., a wound). Significantly, even without water (or other plasticizing agents) preferred embodiments of the gel material of the present invention are flexible.

By "absorbent" it is meant that the material is capable of absorbing fluids, particularly body fluids and preferably moderate to heavy amounts of body fluids, while retaining its structural integrity (i.e., remaining sufficiently intact such that it can perform the function of acting as a wound dressing, for example).

The term hydrophilic is used herein to describe oligomer compositions, which are capable of absorbing water exposed thereto in significant quantity, typically more than about 50% by weight, preferably 100% by weight, more preferably more than 200% by weight.

Preferably the gel material is transparent and retains its transparency after absorption of fluids. By "transparent" it is meant that when the preferred material is applied to a patient (e.g., at a wound site), the area underlying the dressing can be visualized sufficiently to permit observation of the wound by a health care worker.

The application of hydrophilic polymer gels to medical practice is, for example, found in wound dressings, wound packings, adhesives (particularly pressure sensitive adhesives), contact lenses, intraocular lenses, adhesives for biological tissues, adhesion preventing materials, adsorbents for blood purification, base materials for releasing pharmacologic agents, and the like. Materials for dental moldings or impressions are another potential medical article use. Thus, as used herein, "medical" applications encompass dental applications, including dental adhesives, restoratives, coatings, composites, sealants, etc. Because water swelling polymer gels have compositions and mechanical properties similar to those of biological tissues, such gels may be applied in a wide variety of fields in the future.

The ability to vary the crosslink density permits the modification of properties suitable for the various applications described previously. The novel compositions of the present invention cure to form cross linked compositions possessing tailorable properties such as shear, peel, release, strength, hardness, elasticity, absorbancy and toughness, for example, through selection of the particular constituents, and by control of the crosslink density. While the requirements for medical gels and flexible coatings, for example, may be different, the structure of the material and density of linkages can be altered while still maintaining the same method of forming cross linked compositions. The maximum crosslink density is predetermined by the percentage of pulverizable functional groups incorporated into the cross linkable composition. It may also be desirable to partially convert or cure a system for improved processing, while using a subsequent curing stage to obtain final properties.

As used herein, the term "crosslinking" means the formation of a polymeric network of infinite molecular weight and occurs in polymerizations with oligomeric reactants having functionalities greater than two. Additional information may be found in G. Odian, *Principles of Polymerization*, 3rd edition, 1991, John Wiley & Sons: New York, p. 108. A crosslink is formed between the pendent pulverizable functional groups by a chain growth process.

Advantageously, the present invention provides cross linkable compositions that are readily processed without appreciable residual content such as solvents, monomers, plasticizers and/or viscosity modifiers, and which do not contain byproducts from condensation or displacement reactions. Curable systems containing residual content can give rise to a significant increase in density when transformed from the uncured to the cured state causing a net shrinkage in volume. As is well known, shrinkage can cause a general loss of adhesion in many instances as well as significant movement and unpredictable registration. Shrinkage can also create residual stress in coatings, which can subsequently lead to mechanical failure.

The composition of the present invention minimizes shrinkage due to solvent evaporation and/or monomer polymerization. The low shrinkage compositions of this invention are particularly useful in dental, molding applications or in any applications where accurate molding and/or registration is required. The present invention provides a new class of reactive obligers that may be formulated as 100% solids, melt processed, cured by actinic radiation means and that exhibit properties that meet or exceed those of solvent-borne or syrup polymers (i.e. polymer compositions in which the polymer is dissolved in unreacted monomer). The present invention provides compositions that exhibit less than 2% shrinkage, and preferably less than 1%.

Further, the purity of the materials and clean environment for processing are also important to produce high performance materials. Polymers used for coatings and gels are often desirably delivered without significant amounts of volatile materials (such as monomeric species or other residuals) to eliminate any contamination. However, the problems of residual volatile materials constitute a much more formidable challenge especially when acceptable limits of migratable, volatile impurities are on the order of a few parts per million. Industries such as medical and food packaging require materials of high purity and lower cost. The composition of the present invention avoids problems due to residuals contamination, having a residuals content of less than 2 weight percent, preferably less than one weight percent.

DETAILED DESCRIPTION OF THE INVENTION

The present invention provides cross linkable compositions useful in the preparation of hydrophilic gels. The compositions are prepared from obligers having pendent pulverizable functional groups and pendent hydrophilic ploy (alkenylene oxide) groups, and optionally pendent photoinitiator groups, and are formed from ethylenically unsaturated monomers. The composition comprises:

a) a first component oligomer comprising a plurality of polymerized monomer units having pendent hydrophilic ploy(alkenylene oxide) groups, and pendent free-radically pulverizable functional groups; and b) a hydrophilic ploy(alkenylene oxide) crosslinking agent having pulverizable, ethylenically unsaturated terminal groups.

The composition comprises, per 100 parts by weight of a first component oligomer, a sufficient amount of said crosslinking agent to provide greater than two crosslinks per first component oligomer chain when cured or cross linked. The relative amounts of said first component obligers and said crosslinking agent may vary widely; i.e. from 50 to 99.9 parts by weight, preferably 80 to 99.9 parts by weight, of the first component oligomer and from 0.1 to 50 parts by weight of the crosslinking agent, preferably 0.1 to 20 parts by weight. Generally the amount of said crosslinking agent is ten parts by weight or less. However, the relative amounts are chosen so that the cross linked composition is hydrophilic, i.e. absorbs at least 50 wt. % water.

In one embodiment the crosslinking agent is of the formula:

Z-Q-CH(R$^1$)—CH$_2$—O—(CH(R$^1$)—CH$_2$—O)$_m$—CH(R$^1$)—CH$_2$-Q-Z, wherein Z is a pulverizable ethylenically unsaturated moiety, R$^1$ is a H or a C$_1$ to C$_4$ alkyl group, and m is from 20 to 500, preferably 150 to 400, and Q is a divalent linking group selected from —O—, —NR$^1$—, —CO$_2$— and —CONR$^1$—.

In one embodiment the first oligomer component (a) comprises:

It will be understood with respect to the above description, that the first component oligomer may comprise polymerized monomer units having pendent pulverizable groups and monomer units having pendent photoinitiator groups. Where the obligers comprise both polymerized monomer units having pendent pulverizable groups and monomer units having pendent photoinitiator groups, the total may comprise from 0.1 to 25 parts by weight, preferably 0.1 to 10 parts by weight.

The first component oligomer comprises polymerized monomer units derived from of an ethylenically-unsaturated monomer having pendent ploy(alkenylene oxide) group of the formula:

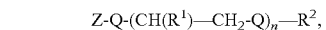

wherein Z is a pulverizable ethylenically unsaturated moiety, R$^1$ is a H or a C$_1$ to C$_4$ alkyl group, R$^2$ is a H, a C$_1$ to C$_4$ alkyl group, aryl group, or combinations thereof and n is from 2 to 100, preferably 5 to 20, and Q is a divalent linking group selected from —O—, —NR$^1$—, —CO$_2$— and —CONR$^1$—. The oligomer comprises from 20 to 99 parts by weight, preferably 50 to 90 parts by weight, of such monomer units.

In one embodiment, the ploy(alkenylene oxide) group is a ploy(ethylene oxide) (co)polymer. In another embodiment, the pendent ploy(alkenylene oxide) group is a ploy(ethylene oxide-co-propylene oxide) copolymer. Such copolymers may be block copolymers, random copolymers, or gradient copolymers.

Useful ethylenically unsaturated moiety, Z, of the monomer may include:

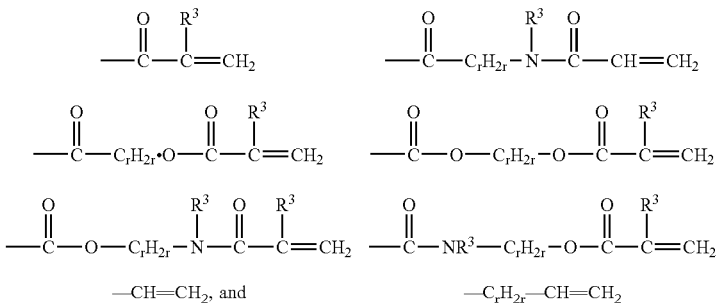

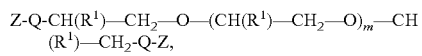

a) from 20 to 99 parts by weight, preferably 50 to 90 parts by weight, of polymerized monomer units having pendent, hydrophilic ploy(alkenylene oxide) groups, and b) from 0.1 to 25 parts by weight, preferably 0.1 to 10 parts by weight, of polymerized monomer units derived from of an ethylenically-unsaturated monomer having a pendent pulverizable group; and c) from 0 to 25 parts by weight, preferably 0.1 to 10 parts by weight, of polymerized monomer units derived from of an ethylenically-unsaturated monomer having a pendent photoinitiator group; and d) from 0 to 30 parts by weight, preferably less than 15 parts by weight, of polymerized monomer units derived from acrylic acid esters, preferably of non-tertiary alkyl alcohols containing 1-14 carbon atoms; and e) from 0 to 35 parts by weight, preferably less than 25 parts by weight, of at least one other monomer (described below).

wherein R$^3$ is H or Me and r=1-10.

The monomer having a ploy(alkenylene oxide) group can be prepared, for example, by reacting mono- or di-functional alkenylene oxide (co)polymers (which are typically commercially available) with reactive ethylenically unsaturated compounds (e.g., acrylates). The functional groups terminating the ploy(alkenylene oxide) may include hydroxy groups, amine groups and carboxy groups. A variety of reactive ethylenically unsaturated compounds such as acrylate derivatives can be used including, but not limited to, (meth)acrylic acid, (meth)acryloyl chloride, (meth)acrylic anhydride, and 2-isocyanatoethyl (meth)acrylate. Preferably, the monomer is prepared by reacting the mono- or di-functional alkenylene oxide (co)polymer with (meth) acrylic anhydride. Typically, if a stoichiometric amount of the ethylenically unsaturated reactant is combined with the monofunctional alkenylene oxide (co)polymer (such as a monohydroxy terminated alkenylene oxide (co)polymer), 100% conversion to the monosubstituted product is obtained.

Examples of suitable monofunctional ploy(alkenylene oxide) monomers include ploy(ethylene oxide) (meth)acrylate, ploy(propylene oxide) (meth)acrylate, ploy(ethylene oxide-propylene oxide) (meth)acrylate, and combinations thereof. Such monomers preferably include one nonreactive end group such as ($C_1$-$C_4$)alkoxy, aryloxy (e.g., phenoxy), and ($C_1$-$C_4$)alkaryloxy. These groups can be linear or branched. These monomers can be of a wide range of molecular weights and are commercially available from sources such as Sartomer Company, Exton, Pa.; Shinnakamura Chemical Co., Ltd., Tokyo, Japan; Aldrich, Milwaukee, Wis.; and Osaka Organic Chemical Ind., Ltd., Osaka, Japan.

The first component obligers of the composition comprise one or more pendent groups that include free-radically pulverizable unsaturation, including (meth)acryloyl, (meth)acryloxy, propargyl, vinyl, allyl, acetylenyl and (meth)acrylamido. Such pendent groups can be incorporated into the oligomer in at least two ways. The most direct method is to include among the monomer units monomers having two or more free radically pulverizable groups, preferably of differing reactivity. The oligomer may comprise 0.1 to 25 parts by weight, preferably 0.1 to 10 parts by weight, of such monomer units.

Using the "direct method" of incorporating the pendent, free-radically pulverizable functional group, useful functional monomers include those unsaturated aliphatic, cycloaliphatic, and aromatic compounds having up to about 36 carbon atoms that include a functional group capable of free radical addition such as those groups containing a carbon-carbon double bond including vinyl, vinyloxy, (meth)acrylic, (meth)acrylamido, and acetylenic functional groups.

Examples of polyethylenically unsaturated monomers that can be used include, but are not limited to, polyacrylic-functional monomers such as ethylene glycol diacrylate, propylene glycol dimethacrylate, bisphenol-A di(meth)acrylate, trimethylolpropane triacrylate, 1,6-hexanedioldiacrylate, pentaerythritol di-, tri-, and tetraacrylate, and 1,12-dodecanedioldiacrylate; olefinic-acrylic-functional monomers such as allyl methacrylate, 2-allyloxycarbonylamidoethyl methacrylate, and 2-allylaminoethyl acrylate; allyl 2-acrylamido-2,2-dimethylacetate; divinylbenzene; vinyloxy group-substituted functional monomers such as 2-(ethenyloxy)ethyl (meth)acrylate, 3-(ethynyloxy)-1-propene, 4-(ethynloxy)-1-butene, and 4-(ethenyloxy)butyl-2-acrylamido-2,2-dimethylacetate, and the like. Useful polyunsaturated monomers, and useful reactive/co-reactive compounds that may be used to prepare a polymer having pendent unsaturation are described in greater detail in U.S. Pat. No. 5,741,543 (Winslow et al.), incorporated in its entirety herein by reference.

Preferred polyunsaturated monomers are those where the unsaturated groups are of unequal reactivity. Those skilled in the art recognize that the particular moieties attached to the unsaturated groups affect the relative reactivities of those unsaturated groups. For example, where a polyunsaturated monomer having unsaturated groups of equal reactivity (e.g., HDDA) is used, premature gelation of the composition must be guarded against by, for example, the presence of oxygen, which acts as a radical scavenger. Conversely, where a polyunsaturated monomer having unsaturated groups of differing reactivities is used, the more reactive group (such as (meth)acrylate or (meth)acrylamido) preferentially is incorporated into the oligomer backbone before the less reactive unsaturated group (such as vinyl, allyl, vinyloxy, or acetylenic) reacts to crosslink the composition. The direct method is generally not preferred due to difficulty in control of branching and premature gellation.

An indirect, but preferred, method of incorporating pendent groups that comprise pulverizable unsaturation into the obligers is to include among the monomer units of the oligomer some that comprise a reactive functional group. Useful reactive functional groups include, but are not limited to, hydroxyl, amino, oxazolonyl, oxazolinyl, acetoacetyl, azlactonyl, carboxyl, isocyanato, epoxy, aziridinyl, acyl halide, and cyclic anhydride groups. Preferred among these are carboxyl, hydroxyl, amino, azlactonyl and aziridinyl groups. These pendent reactive functional groups are reacted with unsaturated compounds that comprise functional groups that are co-reactive with the reactive pendent functional group. When the two functional groups react, an oligomer with pendent unsaturation results. In some applications, it may be desirable to use less than a stoichiometric equivalent of unsaturated compounds that comprise co-reactive functional groups, so that some of the pendent functional groups on the oligomer(s) remain unreacted.

Using the "indirect method" of incorporating the pendent, free-radically pulverizable functional groups, useful reactive functional groups include hydroxyl, secondary amino, oxazolinyl, oxazolonyl, acetyl, acetonyl, carboxyl, isocyanato, epoxy, aziridinyl, acyl halide, vinyloxy, and cyclic anhydride groups. Where the pendent reactive functional group is an isocyanato functional group, the co-reactive functional group preferably comprises a secondary amino or hydroxyl group. Where the pendent reactive functional group comprises a hydroxyl group, the co-reactive functional group preferably comprises a carboxyl, ester, acyl halide, isocyanato, epoxy, anhydride, azlactonyl or oxazolinyl group. Where the pendent reactive functional group comprises a carboxyl group, the co-reactive functional group preferably comprises a hydroxyl, amino, epoxy, isocyanate, or oxazolinyl group. Most generally, the reaction is between a nucleophile and electrophic functional groups.

Representative examples of useful monomers having reactive functional groups include hydroxyalkyl (meth)acrylates such as 2-hydroxyethyl (meth)acrylate, 3-hydroxypropyl (meth)acrylate, 2,3-dihydroxypropyl (meth)acrylate, 4-hydroxybutyl (meth)acrylate and 2-(2-hydroxyethoxy)ethyl (meth)acrylate; aminoalkyl (meth)acrylates such as 3-aminopropyl (meth)acrylate and 4-aminostyrene; oxazolinyl compounds such as 2-ethenyl-1,3-oxazolin-5-one, 2-vinyl-4,4-dimethyl-1,3-oxazolin-5-one, 2-isopropenyl-4,4-dimethyl-1,3-oxazolin-5-one and 2-propenyl-4,4-dimethyl-1,3-oxazolin-5-one; carboxy-substituted compounds such as (meth)acrylic acid and 4-carboxybenzyl (meth)acrylate; isocyanato-substituted compounds such as isocyanatoethyl (meth)acrylate and 4-isocyanatocyclohexyl (meth)acrylate; epoxy-substituted compounds such as glycidyl (meth)acrylate; aziridinyl-substituted compounds such as N-acryloylaziridine and 1-(2-propenyl)-aziridine; and acryloyl halides such as (meth)acryloyl chloride.

Preferred functional monomers have the general formula:

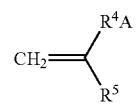

wherein $R^5$ is hydrogen, a $C_1$ to $C_4$ alkyl group, or a phenyl group, preferably hydrogen or a methyl group; $R^4$ is a single bond or a divalent linking group that joins an ethylenically unsaturated group to a reactive functional group "A" and preferably contains up to 34, preferably up to 18, more preferably up to 10, carbon and, optionally, oxygen and nitrogen atoms and, when $R^4$ is not a single bond, is preferably selected from

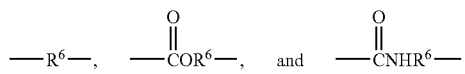

in which $R^6$ is an alkenylene group having 1 to 6 carbon atoms, a 5- or 6-membered cycloalkylene group having 5 to 10 carbon atoms, or an alkenylene-oxyalkylene in which each alkenylene includes 1 to 6 carbon atoms or is a divalent aromatic group having 6 to 16 carbon atoms; and A is a functional group, capable of reacting with a co-reactive functional group for the incorporation of a free-radically pulverizable functional group.

The first component oligomer may include monomer units derived from ethylenically unsaturated monomers having a photoinitiator group in addition to monomer units having free-radically pulverizable unsaturation. The oligomer may comprise 0 to 25 parts by weight, preferably 0.1 to 10 parts by weight, of such monomer units, based on the total weight of the oligomer. Where the obligers comprise both polymerized monomer units having a pendent pulverizable groups and monomer units having a pendent photoinitiator groups, the total may comprise from 0.1 to 25 parts by weight, preferably 0.1 to 10 parts by weight.

Ethylenically unsaturated monomers that comprise photoinitiator group, preferably an α-cleaving photoinitiator group and that are copolymerizable with the aforementioned free radically-pulverizable ethylenically unsaturated monomers (hereinafter "photoinitiator monomers") constitute from about 0.01 to about 20 pbw, preferably 0.01 to 8 pbw, of the cross linkable composition. Preferred photoinitiator monomers include free-radically pulverizable, ethylenically unsaturated compounds having the functionality represented by the structure:

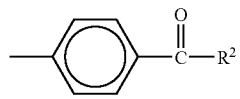

wherein $R^2$ is

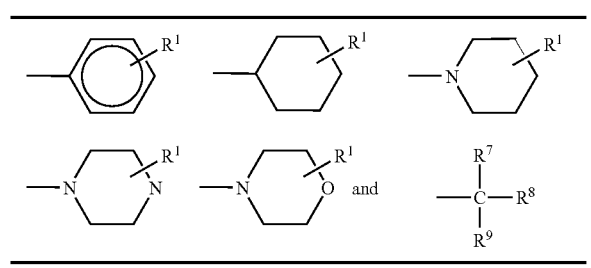

wherein $R^1$ is H or a $C_1$ to $C_4$ alkyl group, $R^7$, $R^8$ and $R^9$ are independently a hydroxyl group, a phenyl group, a $C_1$ to $C_6$ alkyl group, or a $C_1$ to $C_6$ alkoxy group.

A variety of photoinitiator monomers can be made by reacting an ethylenically unsaturated monomer comprising a first reactive functional group with a compound that comprises a radiation-sensitive group and second reactive functional group, the two functional groups being co-reactive with each other. Preferred co-reactive compounds are ethylenically unsaturated aliphatic, cycloaliphatic, and aromatic compounds having up to 36 carbon atoms, optionally one or more oxygen and/or nitrogen atoms, and at least one reactive functional group. When the first and second functional groups react, they form a covalent bond and link the co-reactive compounds.

Examples of useful reactive functional groups include hydroxyl, secondary amino, oxazolinyl, oxazolonyl, acetyl, acetonyl, carboxyl, isocyanato, epoxy, aziridinyl, acyl halide, and cyclic anhydride groups. Where the pendent reactive functional group is an isocyanato functional group, the co-reactive functional group preferably comprises a secondary amino, carboxyl, or hydroxyl group. Where pendent reactive functional group comprises a hydroxyl group, the co-reactive functional group preferably comprises a carboxyl, isocyanato, epoxy, anhydride, or oxazolinyl group. Where the pendent reactive functional group comprises a carboxyl group, the co-reactive functional group preferably comprises a hydroxyl, amino, epoxy, vinyloxy, or oxazolinyl group.

Representative examples of ethylenically unsaturated compounds having a reactive functional group include hydroxyalkyl (meth)acrylates such as 2-hydroxyethyl (meth)acrylate and 2-(2-hydroxyethoxy)ethyl (meth)acrylate; aminoalkyl (meth)acrylates such as 3-aminopropyl (meth)acrylate and 4-aminostyrene; oxazolinyl compounds such as 2-ethenyl-1,3-oxazolin-5-one and 2-propenyl-4,4-dimethyl-1,3-oxazolin-5-one; carboxy-substituted compounds such as (meth)acrylic acid and 4-carboxybenzyl (meth)acrylate; isocyanato-substituted compounds such as isocyanatoethyl (meth)acrylate and 4-isocyanatoclohexyl (meth)acrylate; epoxy-substituted compounds such as glycidyl (meth)acrylate; aziridinyl-substituted compounds such as N-acryloylaziridine and 1-(2-propenyl)-aziridine; and acryloyl halides such as (meth)acryloyl chloride.

Representative examples of co-reactive compounds include functional group-substituted compounds such as 1-(4-hydroxyphenyl)-2,2-dimethoxyethanone, 1-[4-(2-hydroxyethyl)phenyl]-2,2-dimethoxyethanone, (4-isocyanatophenyl)-2,2-dimethoxy-2-phenylethanone, 1-{4-[2-(2,3-epoxypropoxyophenyl]}-2,2-dimethyl-2-hydroxyethanone, 1-[4-(2-aminoethoxy)phenyl]-2,2-dimethoxyethanone, and 1-[4-(carbomethoxy)phenyl]-2,2-dimethoxyethanone. Such photoinitiator monomers (and polymeric photoinitiators derived therefrom) are described, for example, in U.S. Pat. No. 5,902,836 (Babu et al.) and U.S. Pat. No. 5,506,279 (Babu et al.), the disclosures of which are herein incorporated by reference.

It will be understood, with respect to the above description, that the photoinitiator group may be incorporated into the first component oligomer in at least two ways: the "direct method" whereby a monomer unit having a photoinitiator groups is polymerized with the other component monomers to produce the first component oligomer, or the "indirect method" whereby the oligomer is provided with reactive functional groups, which are subsequently functionalized with a photoinitiator compounds having a co-reactive functional group to produce the first component oligomer.

As an alternative to incorporating a pendent photoinitiator group into the first component oligomer, the photoinitiator may comprise a non-polymeric or non-pulverizable photoinitator. Useful photoinitiators include benzoin ethers such as benzoin methyl ether and benzoin isopropyl ether; substituted acetophenones such as 2,2-diethoxyacetophenone, available as Irgacure™ 651 photoinitiator (Ciba-Geigy Corp.; Ardsley, N.Y.), 2,2-dimethoxy-2-phenyl-1-phenylethanone, available as Esacure™ KB-1 photoinitiator (Sartomer Co.; West Chester, Pa.), and dimethoxyhydroxyacetophenone; substituted α-ketols such as 2-methyl-2-hydroxy propiophenone; such as 2-naphthalene-sulfonyl chloride; such as 1-phenyl-1,2-propanedione-2-(O-ethoxycarbonyl)oxime. Particularly preferred among these are the substituted acetophenones.

Preferred photoinitiators are photoactive compounds that undergo a Norrish I cleavage to generate free radicals that can initiate by addition to the acrylic double bonds. Norrish type 1 photocrosslinkers, especially α-cleavage type photoinitiators, are preferred.

The first component obligers may further comprise alkyl acrylate esters. Alkyl acrylate ester monomers useful in the invention include straight-chain, cyclic, and branched-chain isomers of alkyl esters containing $C_1$-$C_{30}$ alkyl groups. Due to $T_g$ and sidechain crystallinity considerations, preferred alkyl acrylate esters are those having from $C_5$-$C_{12}$ alkyl groups, although use of $C_1$-$C_4$ and $C_{13}$-$C_{14}$ alkyl groups are also useful if the combinations provide a molecule averaged number of carbon atoms between $C_5$ and $C_{12}$. However, for many applications higher, i.e. $C_{12}$-$C_{30}$ alkyl groups may be preferred. Useful specific examples of alkyl acrylate esters include: methyl acrylate, ethyl acrylate, n-propyl acrylate, 2-butyl acrylate, iso-amyl acrylate, n-hexyl acrylate, n-heptyl acrylate, isobornyl acrylate, n-octyl acrylate, iso-octyl acrylate, 2-ethylhexyl acrylate, iso-nonyl acrylate, decyl acrylate, undecyl acrylate, dodecyl acrylate, tridecyl acrylate, and tetradecyl acrylate. The oligomer may comprise 0 to 30 parts by weight of such monomer units. Where present, the oligomer generally comprises less than 15 parts by weight, e.g. 1 to 15 parts by weight of such monomer units.

The first component oligomer may further comprise "other monomers" including "polar monomers". As used herein "polar monomers" are those pulverizable monomers having a water miscibility (water in monomer) of at least 1 wt. %, preferably at least 5 weight % without reaching a cloud point and are exclusive of the ploy(alkenylene oxide) monomer. The oligomer may comprise 0 to 35 parts by weight of such monomer units. Where present, the oligomer generally comprises less than 25 parts by weight, e.g. 1 to 25 parts by weight of such monomer units.

Polar monomers can be used to increase the absorbency and/or improve the mechanical properties (e.g. the tensile strength) of the cross linked polymer used in forming the gel material. Preferred polar monomers can also provide compliance to the resultant polymer. Examples of suitable polar monomers include 2-hydroxyethyl(meth)acrylate (HEMA), 2-hydroxypropyl(meth)acrylate, 3-hydroxypropyl(meth)acrylate, 2,3-dihydroxypropyl (meth)acrylate, 4-hydroxybutly(meth)acrylate, N-vinyl caprolactam, N-vinyl acetamide, N-vinyl pyrrolidone, acrylonitrile, tetrahydrofurfuryl acrylate, acrylamide, mono- or di-N-alkyl substituted acrylamide, (meth)acrylic acid, itaconic acid, beta-carboxyethyl acrylate, glycerol methacrylate, [2-(meth)(acryloyloxy)ethyl]trimethylammonium chloride, [2-(meth)(acryloyloxy)ethyl]trimethylammonium methyl sulfate, and combinations thereof. Preferred polar monomers include 2-hydroxyethyl (meth)acrylate (HEMA), N-vinyl pyrrolidone, N-vinyl acetamide, and mixtures thereof, and the like.

The first component obligers may further comprise other monomers, not previously described. The selection of the "other monomers" useful in preparing the oligomer(s) is such that the ultimate cross linked material has properties suitable for its application. For example, "other monomers" may be used to increase the tensile strength or other mechanical properties, or to control the $T_g$ of the polymer. Representative examples of "other monomers" include free-radically pulverizable monomers having at least one ethylenically unsaturated pulverizable group that are copolymerizable with the aforementioned monomers, and include vinyl monomers such as vinyl acetate, styrenes, allyl ethers, maleic anhydride, and alkyl vinyl ethers.

The obligers used in forming the hydrophilic, cross linkable composition of the present invention can be produced by polymerizing the above-described monomers by conventional polymerization methods. Typical polymerization methods that can be used include thermal and/or photochemical as well as bulk and solution polymerization.

In a typical solution polymerization method, a monomer mixture is heated with stirring in the presence of a solvent and a polymerization initiator. Examples of the solvent are methanol, ethanol, isopropanol, acetone, methyl ethyl ketone, methyl acetate, ethyl acetate, toluene, xylene, and an ethylene glycol alkyl ether. Those solvents can be used alone or as mixtures thereof. Examples of the polymerization initiator are benzoyl peroxide, cumene hydroperoxide, diisopropyl peroxydicarbonate, and 2,2'-azo-bis-isobutyronitrile. Those polymerization initiators can be used alone or as mixtures thereof.

In a typical photopolymerization method, a monomer mixture is irradiated with ultraviolet (UV) rays in the presence of a photopolymerization initiator (i.e., photoinitiators). Preferred photoinitiators are those available under the trade designations IRGACURE and DAROCUR from Ciba Speciality Chemical Corp., Tarrytown, N.Y. and include 1-hydroxy cyclohexyl phenyl ketone (IRGACURE 184), 2,2-dimethoxy-1,2-diphenylethan-1-one (IRGACURE 651), bis(2,4,6-trimethylbenzoyl)phenylphosphineoxide (IRGACURE 19), 1-[4-(2-hydroxyethoxy)phenyl]-2-hydroxy-2-methyl-1-propane-1-one (IRGACURE 2959), 2-benzyl-2-dimethylamino-1-(4-morpholinophenyl)butanone (IRGACURE 369), 2-methyl-1-[4-(methylthio)phenyl]-2-morpholinopropan-1-one (IRGACURE 907), and 2-hydroxy-2-methyl-1-phenyl propan-1-one (DAROCUR 1173). Particularly preferred photoinitiators are IRGACURE 819, 184 and 2959.

These photo- and thermal initiators can be employed in concentrations ranging from about 0.0001 to about 3.0 pbw, preferably from about 0.001 to about 1.0 pbw, and more preferably from-about 0.005 to about 0.5 pbw, per 100 pbw of the monomer composition.

The first oligomer may be prepared (e.g., by solution polymerization followed by isolation) and then combined with a separately prepared second component. Any residual monomer and/or solvents used in the preparation are generally removed by conventional techniques such as distillation, vacuum evaporation, etc., to reduce the residual content to less than 2 wt. %, prior to crosslinking. Depending on the type of coating process to be used, the relative amounts of the oligomer(s) can vary greatly. The polymerizations may be conducted in the presence of suitable solvents such as ethyl acetate, toluene and tetrahydrofuran that are unreactive with the functional groups of the components of the first and second components.

As previously described, the pendent unsaturated groups of the oligomer may be introduced by either the direct or indirect methods.

Molecular weight may be controlled through the use of chain transfer agents and chain retarding agents, including mercaptans, disulfides, triethyl silane, carbon tetrabromide, carbon tetrachloride, alpha-methyl styrene and others such as are known in the art. Useful chain transfer agents also include cobalt chelates, as described in U.S. Pat. Nos. 4,680,352 and 4,694,054, and oligomeric chain transfer agents as exemplified by

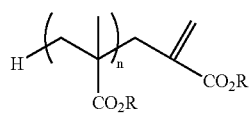

wherein each R is a lower alkyl group or a functional group (as previously described) and n is a number typically less than 10, as described in U.S. Pat. Nos. 5,362,826 and 5,773,534.

Liquid obligers may be obtained if the glass transition temperature of the oligomer component is below ambient temperature and the molecular weight of the oligomer component is below entanglement molecular weight (i.e. a degree of polymerization of less than about 300). Low melting solids may be obtained when the $T_g$ is at or below ambient temperature. Powders may be obtained when the $T_g$ is above ambient temperature. Due to the amount of ploy (alkenylene oxide) in the obligers the obligers are generally low melting solids or liquids.

First component obligers have relatively low molecular weight, then build molecular weight (and strength) by a chain-growth process of the obligers and crosslinking agent, through the pulverizable functional groups. As result of the relatively low molecular weight, the obligers are easily processible in operations such as coating, spraying, extrusion and molding, because of the low melt viscosity prior to crosslinking, and without the need for residuals, such as solvents, plasticizers or viscosity modifiers. With the present obligers, the slope of the log-log plot of viscosity vs. molecular weight ($M_n$) is about 1, whereas for higher molecular weight polymers the slope is 3.4. The obligers of the present invention provide processibility, and then crosslinking of the obligers provides the needed physical properties such as toughness, hardness, tensile strength and others that are manifested in the cured state. Unless otherwise indicated molecular weight will refer to number average molecular weight.

The obligers have an average degree of polymerization (DP) generally less than about 300. The greater than expected viscosity (for polymers having a degree of polymerization greater than 300, is attributed to entanglements of polymer chains. It has been shown empirically that polymers or obligers with less than 300 repeat units are not entangled. Prior to the present invention, unentangled polymers have been shown to be processible but they have low strength.

If desired, higher molecular weight polymers may be blended with lower molecular weight obligers so that the mixture has a viscosity of 500 to 10,000 cPs at temperatures less than 100° C.

The hydrophilic, cross linkable composition further comprises a crosslinking agent of the formula:

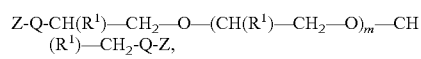

wherein Z is a pulverizable ethylenically unsaturated moiety, $R^1$ is a H or a $C_1$ to $C_4$ alkyl group, and m is from 20 to 500, preferably 150 to 400, and Q is a divalent linking group selected from —O—, —$NR^1$—, —$CO_2$— and —$CONR^1$—.

In one embodiment, the ploy(alkenylene oxide) group is a ploy(ethylene oxide) (co)polymer. In another embodiment, the pendent ploy(alkenylene oxide) group is a ploy(ethylene oxide-co-propylene oxide) copolymer. Such copolymers may be block copolymers, random copolymers, or gradient copolymers.

Useful ethylenically unsaturated moiety, Z, of the monomer may include:

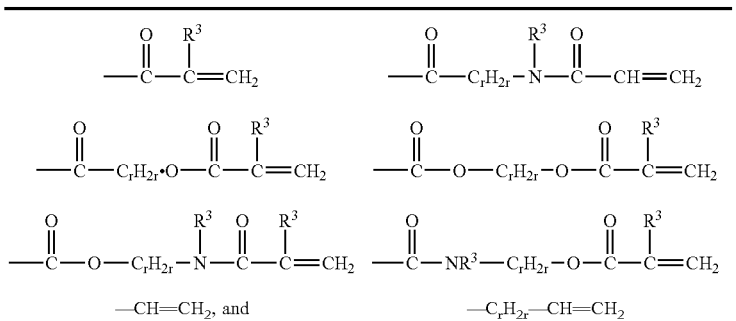

wherein $R^3$ is H or Me and r=1-10.

The crosslinking agent having a ploy(alkenylene oxide) group can be prepared, for example, by reacting di-functional alkenylene oxide (co)polymers (which are typically commercially available) with reactive ethylenically unsaturated compounds (e.g., acrylates). The functional groups terminating the ploy(alkenylene oxide) may include hydroxy groups, amine groups and carboxy groups. A variety of reactive ethylenically unsaturated compounds such as acrylate derivatives can be used including, but not limited to, (meth)acrylic acid, (meth)acryloyl chloride, (meth)acrylic anhydride, and 2-isocyanatoethyl (meth)acrylate. Preferably, the monomer is prepared by reacting the di-functional alkenylene oxide (co)polymer with (meth)acrylic anhydride. Typically, if a stoichiometric amount of the ethylenically unsaturated reactant is combined with the difunctional alkenylene oxide (co)polymer (such as a hydroxy terminated alkenylene oxide (co)polymer), 100% conversion to the disubstituted product is obtained.

Examples of suitable difunctional ploy(alkenylene oxide) monomers include ploy(ethylene oxide) di(meth)acrylate, ploy(propylene oxide) di(meth)acrylate, ploy(ethylene oxide-propylene oxide) di(meth)acrylate, and combinations thereof. These monomers can be of a wide range of molecular weights and are commercially available from sources such as Sartomer Company, Exton, Pa.; Shinnakamura Chemical Co., Ltd., Tokyo, Japan; Aldrich, Milwaukee, Wis.; and Osaka Organic Chemical Ind., Ltd., Osaka, Japan.

As previously described, the composition of the present invention comprises a first oligomer component with a plurality of pendent pulverizable functional groups, and a second crosslinking component with a plurality of terminal, co-reactive pulverizable functional groups and a hydrophilic ploy(alkenylene oxide) group, and optionally a photoinitiator (if the first component oligomer does not contain pendent photoinitiator groups). The amount of each monomer component and the relative amounts of the first and second component obligers may be adjusted to obtain compositions having desired hydrophilicity, melt-processibility and mechanical properties.

A coatable oligomer composition may be prepared by combining the first oligomer component, the crosslinking agent and optionally a photoinitiator (if a photoinitor pendent group is not incorporated into the first component oligomer). Partial conversion of the two components may be desirable to achieve a thickened solution exhibiting a coatable viscosity of from about 500-10,000 cPs at 22° C., more preferably from about 750 to 7500 cPs.

Once configured into the desired construction, the composition including the first oligomer, the crosslinking agent and the optional photoinitiator may be irradiated with activating UV radiation to crosslink the composition. UV light sources can be of two types: 1) relatively low light intensity sources such as blacklights which provide generally 10 mW/cm$^2$ or less (as measured in accordance with procedures approved by the United States National Institute of Standards and Technology as, for example, with a UVIMAP™ UM 365 L-S radiometer manufactured by Electronic Instrumentation & Technology, Inc., in Sterling, Va.) over a wavelength range of 280 to 400 nanometers and 2) relatively high light intensity sources such as medium pressure mercury lamps which provide intensities generally greater than 10 mW/cm$^2$, preferably between 15 and 450 mW/cm$^2$. Where actinic radiation is used to fully or partially crosslink the oligomer composition, high intensities and short exposure times are preferred. For example, an intensity of 600 mW/cm$^2$ and an exposure time of about 1 second may be used successfully. Intensities can range from about 0.1 to about 150 mW/cm$^2$, preferably from about 0.5 to about 100 mW/cm$^2$, and more preferably from about 0.5 to about 50 mW/cm$^2$.

Accordingly, relatively thick coatings (e.g., at least about 0.025 mm) can be achieved when the extinction coefficient of the photoinitiator is low. Coatings from of 0.5 or more mm thick are possible and are within the scope of the present invention.

Additional advantages of the photopolymerization method are that 1) heating the composition is unnecessary and 2) photoinitiation is stopped completely when the activating light source is turned off.

If so desired, measuring the refractive index of the composition material especially in bulk can be used to monitor the extent of polymerization. The refractive index changes linearly with respect to conversion. This monitoring method is commonly applied in polymerization kinetics work. See discussions about the method in, for example, G. P. Gladyshev and K. M. Gibov, *Polymerization at Advanced Degrees of Conversion*, Keter Press, Jerusalem (1970).

When preparing a cross linked composition of the invention, it may be expedient for the initiated polymerization reactions to proceed to virtual completion, i.e., depletion of the pendent pulverizable functional groups and/or pendent photoinitiator groups, at temperatures less than about 70° C. (preferably at 50° C. or less) with reaction times less than 24 hours, preferably less than 12 hours, and more preferably less than 6 hours. These temperature ranges and reaction rates obviate the need for free radical polymerization inhibitors, which are often added to acrylic systems to stabilize against undesired, premature polymerization and gelation. Furthermore, the addition of inhibitors adds residuals that will remain with the system and inhibit the desired polymerization of the oligomer and formation of the cross linked compositions of the invention. Free radical polymerization inhibitors are often required at processing temperatures of 70° C. and higher for reaction periods of more than about 6 hours.

The cross linked composition can be characterized as a polymer having oligomer chains cross linked with at least one hydrophilic ploy(alkenylene oxide) moiety. Thus, during exposure to UV energy, the free radical resulting from the photoinitiator adds to the pendent ethylenically unsaturated moiety (of the oligomer or the crosslinking agent) to form a crosslink between the oligomer chains and crosslinking agent upon coupling or propagation with another pulverizable group. In general, the present cross linked composition has effective molecular weight between crosslinks, ($M_c$), of greater than or equal to 1,000 and preferably greater than 3,000. Effective molecular weight between crosslinks ($M_c$), may be measured by dynamic mechanical analysis.

The degree of crosslinking may be easily controlled by the number and concentration of pendent unsaturated groups, the number and concentration of optional photoinitiator groups that are pendent on the oligomer(s) and the amount of crosslinking agent. Generally the smaller the $M_c$, the lower the elasticity and hence harder the cross linked composition.

When the composition of the invention is used to prepare hydrophilic gel materials for medical applications, the gel can include one or more active agents, such as pharmacologically active agents. Examples include, but are not limited to, growth factors (e.g., TGF, FGF, PDGF, EGF, etc.), antibacterial agents (e.g., penicillins, neomycin sulfate, sulphonamides, sulfadiazine, silver sulfadiazine, trimethoprim, and other antibiotics, as well as povidone iodine, iodine, silver, silver chloride, and chlorhexidine), antifungal agents (e.g., griseofulvin, chlormidazole hydrochloride, clotrimazole, ketoconazole, miconazole, miconazole nitrate, nistatin, and tolnaftate), disinfectants and antiseptics (e.g., benzalkonium chloride, cetalkonium chloride, chlorhexidine gluconate, ethanol, iodine, methylbenzethonium, povidone iodine, isopropanol, silver, silver oxide, silver salts such as silver lactate and silver chloride, triclosan), local anaesthetics (e.g., tetracaine, benzocaine, prilocalne, procaine), debriding agents, anti-inflammatory agents (e.g., indomethacin, ketoprofen, dichlofenac, ibuprofen, etc.), astringents, enzymes, nutrients (e.g., vitamins, minerals, oxygen, etc.), drugs for cataplasms (e.g., menthol, camphor, peppermint, capsicum extract, capsaicin, etc.), and odor absorbing agents (e.g., zeolites, silicates, chitosans, cyclodextrins, etc.). Preferred active agents are antibacterial agents such as povidone iodine, iodine, silver, silver chloride, and chlorhexidine. Active agents can be used alone or as mixtures thereof. They can be added before or after the reaction product of this invention is cured as long as they do not interfere with polymerization of the polymer. Preferably, they are added in an amount or manner that does not interfere with the function or clarity of the finished gel material.

Optionally, the gel material of the present invention can include hydrocolloids, typically in the form of particles, although they are not necessarily preferred since they can diminish the transparency of the gel material. Examples of hydrocolloids include, but are not limited to, natural gums, such as plant exudates (gum arabic, ghatti, karaya, and tragacanth); plant seed gums (guar, locust bean and acacia), seaweed extracts (agar, algin, alginate salts and carrageenin), cereal gums (starches and modified starches), fermentation or microbial gums (dextran and xanthan gum), modified celluloses (hydroxymethylcellulose, microcrystalline cellulose and carboxymethylcellulose) pectin, gelatin, casein and synthetic gums (polyvinylpyrrolidone, low methoxyl pectin, propyleneglycol alginates, carboxymethyl locust bean gum and carboxymethyl guar gum) and like water-swellable or hydratable hydrocolloids. The term hydrocolloid is used regardless of the state of hydration. The gel material of the present invention preferably includes an amount of the hydrocolloid such that the material is transparent (preferably, the total light transmittance is greater than 84% per ASTM D1003-00). Typically, the amount of hydrocolloid, if used, is less than about 5 wt-%, based on the total weight of the gel material.

Other additives that can be incorporated into the gel material of the present invention include: viscosity modifiers (e.g., polymeric thickeners such as that commercially available under the trade designation GANTREZ resin from International Specialty Products, Wayne, N.J.); chain transfer or retarding agents (e.g., such as alkyl mercaptans such as dodecyl mercaptan, isooctyl thioglycolate, and alpha-methylstyrene, the latter of which can also be a hydrophobic monomer as discussed above); colorants; indicators; tackifiers; plasticizers (e.g., water, glycerin, polyethylene oxide, polypropylene oxide, and mixtures thereof such as those commercially available under the trade designation PLURONICS from BASF Co., as well as various low molecular compounds capable of plasticizing the polymer); antioxidants; etc. Such additives can be added either before or after the polymerization using techniques known to one of skill in the art. Preferably, if used, they can be added in an amount and manner that does not interfere with the function or clarity of the gel material.

Preferably, the gel material of the present invention is substantially free of residuals, including water. This is advantageous at least because special packaging is not required. Furthermore, residuals can migrate to other parts of a dressing, for example, which can be detrimental to the integrity of the dressing, or into the body of the patient on which the dressing is disposed.

Optionally, the gel material may have a patterned surface on at least one major surface thereof. The patterned surface allows greater surface area for absorption of wound exudate when oriented toward the wound surface, while reducing the absorbent surface area in direct or indirect contact with the wound. More significantly, the patterned surface reduces the propensity of the absorbent layer to swell and push against the wound, avoids mushrooming (i.e. expansion of the gel layer through a porous film) and further avoids premature separation of an adhesive layer from the skin.

The optional pattern imparted to the surface of a layer of the gel material may be any suitable preselected three-dimensional pattern. Preferably, the pattern is one that increases the surface area available for absorption and reduces swelling into the wound, retards mushrooming, and/or enhances integrity of the material upon hydration. The pattern can include an array of pattern elements that include, but are not limited to, ridges, channels, mounds, peaks, hemispheres, pyramids, cylinders, cones, blocks, and truncated variations and combinations thereof. The pattern may further include apertures having a predetermined shape and size extending through the thickness of the absorbent layer.

The specific pattern element is advantageously chosen to present minimal surface area in contact with a wound or the facing film if present. The minimal surface area further retards the tendency of the gel material to swell into the wound, mushroom, or adhere to the wound site. Especially useful elements include pyramids, cones and truncated versions thereof, and ridges that are triangular in cross section. The elements may be random or non-random in the x direction, the y direction, or both. For ease of manufacture, it is preferable that the pattern comprises a non-random array of elements disposed on the surface of the gel.

If desired, a pattern may also be imparted to the outer face of the gel layer (i.e., the major surface of the gel layer that faces away from the wound surface). Imparting such a pattern increases the surface area of the gel layer and may promote greater evaporation of the fluid from the gel material. The pattern may be the same or different than the pattern on the facing surface of the gel material, as can the size of the pattern elements. Further, the individual elements on either surface of the gel material may be protuberances extending form the surface, or may be depressions in the surface.

An optional patterned surface may be imparted to the gel material by conventional molding techniques. Alternatively, a desired pattern may be imparted using an embossing technique. Examples of such techniques are described in U.S. Pat. No. 6,566,575, (Stickels et al.), incorporated herein by reference.

If desired, the gel material may be in direct contact with the wound and/or skin surface. However, direct contact may be provided by other suitable hydrocolloid and hydrogel absorbent materials as well.

In a preferred medical article, the gel material forms a layer that is generally about 250 micrometers (i.e., microns) to about 5000 micrometers in total thickness.

Optionally, a wound dressing of the invention may include at least two absorbent layers: a first absorbent layer and a second absorbent layer. The first absorbent layer is typically more absorbent than the second absorbent layer, and can retain a greater volume of body fluids than the second absorbent layer. The second absorbent layer is positioned such that it is located between the first absorbent layer and the wound. This second absorbent layer provides integrity to the wound dressing and avoids transfer of the first absorbent layer into the wound.

The first absorbent layer typically contains the polymer described above prepared from the oligomeric composition. The second absorbent layer is typically positioned in contact with the first absorbent layer and is typically less absorbent of body fluids than the first absorbent layer. The second absorbent layer can contain the reaction product of an acrylic acid ester of a non-tertiary alcohol having from 4 to 14 carbon atoms; a hydrophilic, ethylenically unsaturated monomer; and a polar, ethylenically unsaturated monomer, although other compositions can be used in the second absorbent layer.

Generally, the second absorbent layer functions as a "barrier" between the first absorbent layer (which may partially "disintegrate" when exudate is unevenly, rapidly absorbed or when it absorbs more than about 500%) and the wound. Preferably the second absorbent layer has adhesive properties (or is a pressure sensitive adhesive) and functions to enhance the overall integrity of the wound dressing. In this regard, the second absorbent layer ties the first absorbent layer to a wound-facing layer (or to the wound itself). By having adhesive properties, this second absorbent layer not only aids in controlling the absorption of exudate, but also physically joins other components of the dressing.

As stated above, the first absorbent layer is typically significantly more absorbent than the second absorbent layer, and preferably has an absorbency at least 100 percent greater than the absorbency of the second absorbent layer. The first absorbent layer preferably absorbs at least 200 percent of its weight after immersion in an isotonic saline solution after 24 hours at room temperature.

A typical wound dressing of the present invention preferably includes a porous or non-porous facing layer to provide a fluid permeable barrier between the wound site and the gel layer. The facing layer allows transport of moisture (i.e. fluid and vapor) from the wound to the gel layer and may isolate the wound from other components of the dressing. The facing layer is preferably soft, flexible, conformable, non-irritating and non-sensitizing. Any of a variety of polymers may be used including polyurethane, polyethylene, polypropylene, polyamide or polyester materials. Further, the facing layer may be in the form of moisture vapor permeable films, perforated films, woven-, non-woven or knit webs or scrims. A preferred facing layer comprises a polyurethane film.

In one useful embodiment, the facing layer is conformable to animal (including human) anatomical surfaces, has a moisture vapor transmission rate (MVTR) of at least 300 grams per square meter per 24 hours at 80% relative humidity differential at 40° C. (per method of U.S. Pat. No. 5,733,570 (Chen et al.)), is impermeable to liquid water throughout substantially its entire imperforate area and contains perforations means for passing wound exudate through the facing layer. This means that the facing layer does not pass liquid water under normal wound treatment conditions except at the places in the facing layer that are positively perforated to allow the exudate to pass into the reservoir.

The preferred moisture vapor transmission rate of the facing layer is at least 600 grams per square meter per 24 hours at an 80% relative humidity differential at 40° C. The facing layer may further comprise a pressure sensitive adhesive layer. The adhesive coated facing layer preferably has the aforesaid MVTR. Therefore, if the facing layer is impermeable to liquid water except for the perforation means, the adhesive can be permeable to liquid water and vice versa. Porous or non-porous facing layers such as perforated polyamide, polyester, polypropylene, polyethylene, polyether-amide, polyurethanes, chlorinated polyethylene, styrene/butadiene block copolymers (KRATON brand thermoplastic rubber, Shell Chemical Company, Houston, Tex.) and ploy(vinyl chloride) and those described in U.S. Pat. No. 3,121,021 (Copeland) that are covered with a pressure sensitive adhesive that is not permeable to liquid water can be used for the facing layer. Optionally these films can be perforated. Additional porous materials include woven and non-woven substrates.

It is preferred that the facing layer have the above mentioned moisture vapor or liquid permeability (1) so that maceration of the skin under the wound dressing does not occur, (2) so that moisture build-up under the facing layer does not cause the facing layer and, therefore, wound dressing to be lifted off the skin, and (3) to enhance proximation of the wound edges. Preferred facing layers are thin polymeric films optionally coated with pressure sensitive adhesive which, in combination, have the above characteristics.

The perforation means in the facing layer are holes or slits or other perforations that conduct the passage of liquid water or wound exudate from the wound into the absorbent layer of the wound dressing. The perforations may additionally extend through an adhesive layer, if the front surface of the facing film (that surface facing toward the wound) is coated with a pressure sensitive adhesive layer.

A backing layer may be present in all of the embodiments of the present invention. Preferably the backing layer is conformable to animal anatomical surfaces, impermeable to liquid water and has a moisture vapor transmission rate of at least 600 grams per square meter per 24 hours at an 80% relative humidity differential at 40° C. The backing layer, in combination with a facing layer, may be constructed to form a reservoir (e.g., a pouch or envelope) that surrounds the gel layer, into which the exudate from the wound passes. This reservoir does not permit liquid water or exudate to pass out of it. Instead, the gel layer absorbs the exudate, and moisture in the exudate passes through the backing layer in a vapor form into the atmosphere. The reservoir dressing permits wound exudate to be rapidly removed from the wound site and prevents liquids or bacteria from outside the dressing to contaminate the wound site.

In order to remove moisture vapor, the moisture vapor transmission rate of the backing layer is at least as above noted, and preferably at least 1200 grams per square meter per 24 hours at an 80% relative humidity differential at 40° C.

The preferred embodiments for the facing and backing layers are thin conformable polymeric films. Generally the films are about 12 microns to about 50 microns in thickness, preferably about 12 microns to about 25 microns. Conformability is somewhat dependent on thickness, thus the thinner the film the more conformable the film. Reference has been made herein to the films utilized in the medical article (e.g., wound dressing) of the present invention being conformable to animal anatomical surfaces. This means that when the films of the present invention are applied to an animal anatomical surface, they conform to the surface even when the surface is moved. The preferred films are conformable to animal anatomical joints. When the joint is flexed and then returned to its unflexed position, the film stretches to accommodate the flexation of the joint but is resilient enough to continue to conform to the joint when the joint is returned to its unflexed condition.

Examples of films which are useful in applicant's invention as facing or backing layers include polyurethanes such as those available under the trade designation ESTANE from B. F. Goodrich, Cleveland, Ohio, elastomeric polyester such as those available under the trade designation HYTREL from E. I. duPont deNemours & Co., Wilmington, Del., blends of polyurethanes and polyesters, polyvinyl chlorides, and polyether-amide block copolymers such as those available under the trade designation PEBAX available from Elf-Atochem. Particularly preferred films for use in the present invention are polyurethane and elastomeric polyester films. The polyurethane and elastomeric polyester films exhibit a resilient property that allows the films to have good conformability.

Particularly useful films include "spyrosorbent" films having a differential moisture vapor transmission rate (MVTR). Dressings incorporating spyrosorbent films not only manage wound exudate by absorption, but have the ability to adjust the moisture vapor transmission properties in response to the amount of exudate. Such spyrosorbent films are hydrophilic, moisture vapor permeable and have a relatively high MVTR (wet), and have a differential MVTR ratio (wet to dry) that is greater than 1, and preferably greater than 3:1. The dry MVTR is greater than about 2600 g/m$^2$/24 hrs, preferably about 3000 to 4000 g/m$^2$/24 hrs. A particularly preferred spyrosorbent film, useful as a backing layer, is a segmented polyurethane such as a segmented polyether polyurethane urea based on polytetramethylene glycol and polyethylene glycol polyols. Such a spyrosorbent films are described in U.S. Pat. Nos. 5,653,699 and 4,849,458 (Reed et al.).

Another suitable backing layer is a fluid control film having at least one microstructures-bearing surface with channels that permit directional control of a liquid. This film can be used to transport a fluid to a remote site and thereby facilitate wicking away of a fluid (e.g., wound exudate). Such a film is disclosed in U.S. Pat. No. 6,420,622 (Johnston et al.).

Many different constructions of a wound dressing are possible with the facing layer, the gel layer, and the backing layer. In one embodiment, the areas of the facing layer and the backing layer are greater than that of the gel layer and the facing layer is bonded to the backing layer, thereby forming a pouch, with the gel disposed between the two. In another embodiment, one of the facing or backing layers may be substantially the same area as the gel layer, and the other of greater area. The greater area of the facing or backing layer forms a periphery to which an adhesive layer and a release liner may be attached. It will further be understood that the facing and/or backing layer may be attached or bonded to the adjacent surface of the gel layer to form a contiguous layer construction, in which the backing and facing layers may be the same or of greater area than the gel layer. Alternatively, the backing and facing layers may be bonded to each other, and may or may not be bonded to the gel layer. In these last constructions, the gel layer is constrained within a pouch created by the attachment of the facing and backing layers to each other. The layers may be bonded to each other by any conventional means such as adhesives, heat-sealing, or other bonding means.

It is preferred that the facing and backing layers of the medical articles of the present invention be at least translucent and more preferably sufficiently transparent so that the wound site to which they are applied can be viewed through the medical article. It is advantageous to view and evaluate the wound and healing thereof without removal of the wound dressing to avoid unnecessary handling of the wound site and exposure of the wound to the environment, which reduces the likelihood of contamination, and avoids the need to cleanse the wound as would be the case were the dressing to be removed. It is preferred that the dressing be both transparent and colorless so that the color of the wound, exudate, and periwound skin may also be evaluated. Preferred transparent films for use as facing and backing layers that allow visual inspection of the wound site include polyurethane films such as those available under the trade designation ESTANE from B. F. Goodrich, Cleveland, Ohio; elastomeric polyesters such as those available under the trade designation HYTREL from E. I. duPont deNemours & Co., Wilmington, Del.; and, polyether block amides such as those available under the trade designation PEBAX from Elf Altochem North America, Philadelphia, Pa. Other useful films are those describes in U.S. Pat. No. 4,499,896 (Heinecke); U.S. Pat. No. 4,598,004 (Heinecke); and U.S. Pat. No. 5,849,325 (Heinecke et al).

While the facing layer can be attached to the wound by means other than a pressure sensitive adhesive on its surface, it is preferred to use such an adhesive. The presence of the adhesive of the facing layer normally reduces the moisture vapor permeability of the facing layer. Therefore it is preferred that the facing layer is adhesive coated prior to adding a plurality of perforations to the layer. The wound exudate therefore can readily pass through a perforated adhesive coated facing layer. Preferably, both the facing and backing layers are precoated with an adhesive layer to both facilitate bonding of the backing layer to the facing layer (forming a pouch), and bonding of the facing film to the wound site.

The facing layer is normally attached to the wound site by means of adhesive that can be continuous or pattern coated. The preferred adhesive which can be used with the wound dressings of present invention are the normal adhesives which are applied to the skin such as those described in U.S. Pat. No. Re. 24,906 (Ulrich), particularly a copolymer of 96% iso-octyl acrylate units and 4% acrylamide units and a copolymer of 94% iso-octyl acrylate units and 6% acrylic acid units. Other useful adhesives are those described in U.S. Pat. No. 3,389,827 that comprise block copolymers having three or more polymer block structures having a general configuration --A--B--A--- wherein each A is a thermoplastic polymer block with a glass transition temperature above room temperature (i.e., above about 20° C.) having an average molecular weight between about 5000 and 125,000 and B is a polymer block of a conjugated diene having an average molecular weight between about 15,000 and 250,000. Additional examples of useful adhesives are acrylic adhesives such as iso-octyl acrylate/N-vinyl pyrrolidone copolymer adhesives and cross linked acrylate adhesives such as for example those described in U.S. Pat. No. 4,112,213 (Waldman). Inclusion in the adhesive of medicaments is useful for enhancing wound healing and the inclusion of antimicrobial agents such as iodine is useful for preventing infection.

The adhesive may optionally be a microsphere adhesive with low trauma properties as described in U.S. Pat. No. 5,614,310 (Delgado et al.); a fibrous adhesive with low trauma properties as described in U.S. Pat. No. 6,171,985 B1 (Joseph et al.); or have especially good adhesion to wet skin, such as the adhesives described in U.S. Pat. No. 6,198,016 B1 (Lucast et al.), U.S. Pat. No. 6,518,343 (Lucast et al.) and U.S. Pat. No. 6,441,092 (Gieselman); multilayered adhesives as disclosed in U.S. Pat. No. 6,461,467 (Blatchford et al.). A particularly preferred adhesive includes 15 wt-% acrylic acid, 15 wt-% methoxypolyetliylene oxide 400 acrylate, 70 wt-% isooctyl acrylate, prepared according to Example 1 of U.S. Pat. No. 5,849,325 (Heinecke et al).

The adhesive may be chosen to be permeable to water or wound exudate, or the adhesive may be pattern coated on the front surface of the wound dressing (i.e. the surface in contact with the wound site, whether it is the front surface of the facing or backing layers) so as to not impede the flow of exudate to the gel layer, i.e. the adhesive may be coated at the periphery of the wound dressing. Alternatively the adhesive layer may be perforated as described for the facing film to provide a fluid path for the exudate.

A release liner may be attached to the adhesive layer for ease of handling. Examples of release liners are liners made of or coated with polyethylene, polypropylene and fluorocarbons and silicone coated release papers or polyester films. Examples of the silicone coated release papers are POLYSLIK S-8004, 83 pound (135.4 g/m$^2$) bleached silicone release paper supplied by H. P. Smith Co., Chicago, Ill., and 80 pound (130.5 g/m²) bleached two-sided silicone coated paper (2-80-BKG-157) supplied by Daubert Chemical Co., Dixon, Ill.

A wound dressing of the present invention may also include a frame that allows the dressing to be more easily applied to the wound. The frames are made of a relatively rigid material that maintains the shape of the dressing during handling and application to the wound site. The frame is generally releasably adhered to the back surface of the backing film and is removed after application of the wound dressing. Suitable frames are described in U.S. Pat. No. 5,531,855 (Heinecke et al.) and U.S. Pat. No. 5,738,642 (Heinecke et al.).

EXAMPLES

These examples are merely for illustrative purposes only and are not meant to be limiting on the scope of the appended claims. All parts, percentages, ratios, etc. in the examples and the rest of the specification are by weight, unless noted otherwise. Solvents and other reagents used were obtained from Aldrich Chemical Company; Milwaukee, Wis. unless otherwise noted.

Test Methods

Swelling (Uptake) Test

This test is to measure a polymer's ability to swell when placed in a saline solution. A jar was filled with approximately 200 milliliters of 0.9% saline solution. A 3 centimeter diameter disk, with an approximate thickness of 1.1 millimeters, of the polymer film of interest was weighed and the value was recorded as "dry weight". The sample was completely submerged in the 0.9% saline and remained submerged for 24 hours. The sample was removed, allowed to drip for 1 minute, and then it was weighed and the value was recorded as "wet weight". The percent uptake was calculated using the following formula:

100×(Wet weight−Dry weight)/Dry weight=% Uptake

| Table of Abbreviations | |
|---|---|
| Abbreviation or Trade Designation | Description |
| MPEG | poly(ethylene glycol)(400)-acrylate |
| HEMA | 2-hydroxyethyl methacrylate |
| AMS | Alpha-methyl styrene |
| AIBN | 2,2'-azobisisobutyronitrile initiator |
| IEM | 2-isocyanatoethyl methacrylate |
| Release Liner | Release liner of poly(ethylene terephthalate) coated with silicone |
| DBTDL | Dibutyltindilaurate |
| MAA-PEG | MAA-PEG is a 75/25% by weight poly(ethylene oxide)/poly(propylene oxide) diol functionalized with methacrylic anhydride, prepared as described in WO 2003/086493, first preparative example. |

Examples 1A-1L

Part I: Preparation of Photoinitiator Functional Oligomer

In a brown glass bottle, 130 grams (260 mmol) of MPEG, 70 grams (540 mmol) of HEMA, 8 grams (68 mmol) of AMS and 0.8 grams (5 mmol) of AIBN and 200 milliliters of ethyl acetate were combined, sparged with nitrogen for 15 minutes and capped. The sealed glass bottle was shaken in a thermostated temperature bath shaker at 65° C. for 24 hours. Various amounts of IEM and DBTDL (0.3-0.5 mol % based on IEM) were added to portions of the above prepared oligomer/ethyl acetate solution as shown in Table 1 to generate solutions A-D and were stirred at room temperature for 48 hours.

TABLE 1

| Example Solution | % by Weight IEM |
|---|---|
| A | 0.5 |
| B | 1.0 |
| C | 5.0 |
| D | 10.0 |

Part II: Preparation of a Methacrylate Functional Oligomer

Various amounts of MAA-PEG were added to portions of the oligomer/ethyl acetate solution prepared in Part I above as shown in Table 2 to generate solutions E-P and were stirred at room temperature for 48 hours.

TABLE 2

| Example Solution | Solution from Part I | % by Weight MAA-PEG |
|---|---|---|
| E | A | 0.5 |
| F | A | 10 |
| G | A | 20 |
| H | B | 0.5 |
| I | B | 10 |
| J | B | 20 |
| K | C | 0.5 |
| L | C | 10 |
| M | C | 20 |
| N | D | 0.5 |
| O | D | 10 |
| P | D | 20 |

Part III: Preparation and Testing of Films

A portion of each oligomer solution E-P prepared in Part II above was poured onto a Release Liner, dried in 40° C. oven for 16 hours and covered with another Release Liner. These laminates were cured into films by exposing the constructions to UV radiation for 30 minutes. The Swelling Test Method described above was used to determine the swelling of each film. These results are shown in Table 3.

TABLE 3

| Example Film | Methacrylate functional Oligomer Solution used | Uptake (% by Weight) | Film Appearance Pre-Swelling | Film Appearance Post-Swelling |
|---|---|---|---|---|
| 1A | E | 345 | clear | clear |
| 1B | F | 404 | clear | clear |
| 1C | G | 460 | clear | clear |
| 1D | H | 337 | clear | clear |
| 1E | I | 210 | clear | clear |
| 1F | J | 405 | clear | clear |
| 1G | K | 139 | clear | clear |
| 1H | L | 134 | clear | clear |
| 1I | M | 235 | clear | clear |
| 1J | N | 71 | clear | clear |
| 1K | O | 80 | clear | cloudy |
| 1L | P | 132 | clear | cloudy |

The invention claimed is:

1. A hydrophilic, crosslinkable oligomer composition comprising
   a) a first component oligomer comprising a plurality of polymerized monomer units having pendent hydrophilic poly(alkylene oxide) groups of the formula:

$$Z\text{-}Q\text{-}(CH(R^1)\text{---}CH_2\text{-}Q)_n\text{-}R^2,$$

wherein Z is a polymerizable ethylenically unsaturated moiety, $R^1$ is a H or a $C_1$ to $C_4$ alkyl group, $R^2$ is a H, a $C_1$ to $C_4$ alkyl group, aryl group, or combinations thereof and n is from 2 to 100, and Q is a divalent linking group selected from —O—, —$NR^1$—, —$CO_2$— and —$CONR^1$—, and a plurality of polymerized ethylenically-unsaturated monomer units having pendent, ethylenically unsaturated free-radically polymerizable functional groups; and
   b) a hydrophilic poly(alkylene oxide) crosslinking agent having polymerizable, ethylenically unsaturated terminal groups.

2. The composition of claim 1 wherein said crosslinking agent is of the formula $$Z\text{-}Q\text{-}CH(R^1)\text{---}CH_2\text{---}O\text{---}(CH(R^1)\text{---}CH_2\text{---}O)_m\text{---}CH(R^1)\text{---}CH_2\text{-}Q\text{-}Z,$$

wherein Z is a polymerizable ethylenically unsaturated moiety, $R^1$ is a H or a $C_1$ to $C_4$ alkyl group, and m is from 20 to 500, and Q is a divalent linking group selected from —O—, —$NR^1$—, —$CO_2$— and —$CONR^1$—.

3. The oligomer composition of claim 1 wherein the composition is melt-processable at temperatures of 100° C. or less.

4. The composition of claim 1 wherein said composition has a residual monomer and solvent content of less than 2 weight %.

5. The composition of claim 1, wherein said oligomer a) has an average degree of polymerization of less than 300.

6. The composition of claim 1, wherein said crosslinking agent is a poly(ethylene oxide) (co)polymer.

7. The composition of claim 1, wherein said crosslinking agent is a poly(ethylene oxide-co-propylene oxide) copolymer.

8. The composition of claim 1 wherein said first component oligomer comprises:
   a) from 20 to 99 parts by weight of polymerized ethylenically-unsaturated monomer units having pendent, hydrophilic poly(alkylene oxide) groups, and
   b) from 0.1 to 25 parts by weight of polymerized ethylenically-unsaturated monomer units having a pendent, ethylenically unsaturated polymerizable group; or
   c) from 0 to 25 parts by weight of polymerized ethylenically-unsaturated monomer units having a pendent photoinitiator group; and
   d) from 0 to 30 parts by weight of polymerized ethylenically-unsaturated monomer units derived from acrylic acid esters; and
   e) from 0 to 35 parts by weight of at least one other ethylenically-unsaturated monomer.

9. The composition of claim 1 wherein said first oligomer having pendent unsaturated polymerizable groups is prepared by the reaction of an oligomer having a plurality of pendent reactive functional groups with an unsaturated compounds having co-reactive functional groups.

10. The composition of claim 9 wherein said pendent reactive functional groups are selected from hydroxyl, amino, oxazolinyl, oxazolonyl, acetyl acetonyl, carboxyl, isocyanato, epoxy, aziridinyl, acyloyl halide, and cyclic anhydride groups.

11. The composition of claim 1 which comprises an amount of said crosslinking agent is sufficient to provide more than two crosslinks per first component oligomer chain.

12. The composition of claim 1 which comprises:
   a) from 80 to 99.9 parts by weight of said first component oligomer, and
   b) from 0.1 to 50 parts by weight of said crosslinking agent,
   wherein the composition, when cross linked, can absorb at least 50 wt. % water.

13. The composition of claim 1 further comprising a non-polymeric photoinitiator.

14. A cross linked composition comprising the composition of claim 1, having an average molecular weight between crosslinks of at least 1000.

15. The composition of claim 2, wherein said Z of said crosslinking agent is selected from

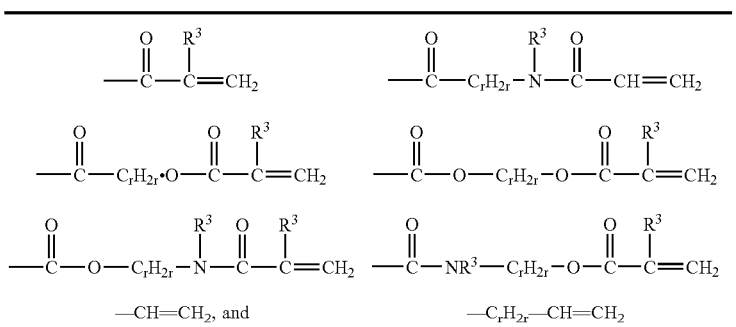

wherein $R^3$ is H or Me and r=1-10.

16. A process for making a substrate bearing a coating of a cross linked polymer composition on at least one surface thereof, comprising the steps of:
   a) coating onto said substrate the oligomer composition of claim 1; and
   b) photochemically crosslinking said first component oligomer and crosslinking agent, in the presence of a photo initiator.

17. The process of claim 16 wherein said oligomer composition has been partially cured to a viscosity of from 750 to 7,500 cPs at 22° C. prior to step a.

18. The process of claim 16 wherein said oligomer composition comprises
a) per 100 parts by weight of said first component, an amount of said crosslinking agent sufficient to provide more than two crosslinks per first component oligomer chain;
b) less than 2 parts by weight residual monomer and solvent content; and
c) from 0.01 to about 5.0 parts by weight of a photoinitiator.

19. The process of claim 16 wherein said first component oligomer comprises:
a) from 20 to 99 parts by weight of polymerized ethylenically-unsaturated monomer units having pendent, hydrophilic poly(alkylene oxide) groups, and
b) from 0.1 to 25 parts by weight of polymerized ethylenically-unsaturated monomer units having a pendent, ethylenically unsaturated polymerizable group; and
c) from 0 to 25 parts by weight of polymerized ethylenically-unsaturated monomer units having a pendent photoinitiator group; and
d) from 0 to 30 parts by weight of polymerized acrylic acid esters; and
e) from 0 to 35 parts by weight of at least one other ethylenically-unsaturated monomer.

20. The process of claim 16 wherein the molecular weight ($M_n$) of said first oligomer is less than the entanglement molecular weight.

21. The process of claim 16 wherein the average degree of polymerization of the first and second component obligers is $\leq 300$.

22. The process of claim 16 wherein said first component oligomer further comprises pendent photoinitiator groups.

23. The process of claim 16 wherein said photoinitiator comprises a separate, component.

24. An absorbent dressing comprising a cross linked hydrophilic gel absorbent layer of claim 1.

25. The absorbent dressing of claim 24 comprising:
a permeable facing layer,
a backing layer bonded to said facing layer at the periphery, and
a hydrophilic gel absorbent layer disposed between the backing and facing layer.

26. The absorbent dressing of claim 24 having a layer of pressure sensitive adhesive on at least a portion of the front surface of the facing layer.

27. The absorbent dressing of claim 24 wherein the gel layer further comprises a pharmacologically active agent.

28. The absorbent dressing of claim 24 wherein the gel layer further comprises a hydrocolloid.

29. The absorbent dressing of claim 24 wherein the gel layer further comprises a patterned surface.

30. The absorbent dressing of claim 24, wherein said absorbent layer is transparent on swelling.

31. The composition of claim 9, wherein the oligomer is derived from monomer units of the formula

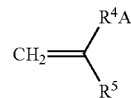

wherein $R^5$ is hydrogen, a $C_1$ to $C_4$ alkyl group, or a phenyl group, preferably hydrogen or a methyl group;
$R^4$ is selected from

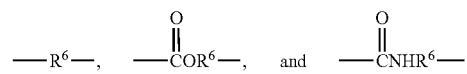

where $R^6$ is an alkylene group having 1 to 6 carbon atoms, or a 5- or 6-membered cycloalkylene group having 5 to 10 carbon atoms, and
A is a reactive functional group, capable of reacting with a co-reactive functional group for the incorporation of a free-radically polymerizable functional group.

UNITED STATES PATENT AND TRADEMARK OFFICE
CERTIFICATE OF CORRECTION

| | | |
|---|---|---|
| PATENT NO. | : 7,342,047 B2 | |
| APPLICATION NO. | : 10/792238 | |
| DATED | : March 11, 2008 | |
| INVENTOR(S) | : Kevin M. Lewandowski | |

It is certified that error appears in the above-identified patent and that said Letters Patent is hereby corrected as shown below:

Title Page,
Item [57], in "Abstract", line 3, delete "obligers" and insert -- oligomers --, therefor.

Item [57], in "Abstract", lines 3-4, delete "ploy(alkenylene" and insert -- poly(alkylene --, therefor.

Item [57], in "Abstract", line 4, delete "pulverizable" and insert -- polymerizable --, therefor.

Item [57], in "Abstract", line 5, delete "ploy(alkenylene" and insert -- poly(alkylene --, therefor.

Column 2,
Line 4, delete "obligers," and insert -- oligomers, --, therefor.

Line 15, delete "ploy(alkenylene" and insert -- poly(alkylene --, therefor.

Line 16, delete "pulverizable" and insert -- polymerizable --, therefor.

Lines 18-19, delete "pulverizable" and insert -- polymerizable --, therefor.

Lines 19-20, delete "ploy(alkenylene" and insert -- poly(alkylene --, therefor.

Line 29, delete "ploy(alkenylene" and insert -- poly(alkylene --, therefor.

Line 30, delete "pulverizable" and insert -- polymerizable --, therefor.

Line 31, delete "ploy(alkenylene" and insert -- poly(alkylene --, therefor.

Line 32, delete "pulverizable," and insert -- polymerizable, --, therefor.

Line 67, delete "obligers" and insert -- oligomers --, therefor.

UNITED STATES PATENT AND TRADEMARK OFFICE
CERTIFICATE OF CORRECTION

PATENT NO. : 7,342,047 B2
APPLICATION NO. : 10/792238
DATED : March 11, 2008
INVENTOR(S) : Kevin M. Lewandowski It is certified that error appears in the above-identified patent and that said Letters Patent is hereby corrected as shown below:

<u>Column 4,</u>
Line 3, delete "pulverizable" and insert -- polymerizable --, therefor.

Line 13, delete "pulverizable" and insert -- polymerizable --, therefor.

Line 34, delete "obligers" and insert -- oligomers --, therefor.

Line 63, delete "obligers" and insert -- oligomers --, therefor.

Line 64, delete "pulverizable" and insert -- polymerizable --, therefor.

Lines 64-65, delete "ploy(alkenylene" and insert -- poly(alkylene --, therefor.

<u>Column 5,</u>
Line 3, delete "ploy(alkenylene" and insert -- poly(alkylene --, therefor.

Line 4, delete "pulverizable" and insert -- polymerizable --, therefor.

Line 5, delete "ploy(alkenylene" and insert -- poly(alkylene --, therefor.

Line 6, delete "pulverizable," and insert -- polymerizable, --, therefor.

Line 12, delete "obligers" and insert -- oligomers --, therefor.

Line 26, delete "pulverizable" and insert -- polymerizable --, therefor.

Line 51, delete "ploy(alkenylene" and insert -- poly(alkylene --, therefor.

Line 55, delete "pulverizable" and insert -- polymerizable --, therefor.

UNITED STATES PATENT AND TRADEMARK OFFICE
CERTIFICATE OF CORRECTION

| | |
|---|---|
| PATENT NO. | : 7,342,047 B2 |
| APPLICATION NO. | : 10/792238 |
| DATED | : March 11, 2008 |
| INVENTOR(S) | : Kevin M. Lewandowski |

It is certified that error appears in the above-identified patent and that said Letters Patent is hereby corrected as shown below:

<u>Column 6,</u>
Line 3, delete "pulverizable" and insert -- polymerizable --, therefor.

Line 5, delete "obligers" and insert -- oligomers --, therefor.

Line 6, delete "pulverizable" and insert -- polymerizable --, therefor.

Line 12, delete "ploy(alkenylene" and insert -- poly(alkylene --, therefor.

Line 16, delete "pulverizable" and insert -- polymerizable --, therefor.

Line 24, delete "ploy(alkenylene" and insert -- poly(alkylene --, therefor.

Line 25, delete "ploy(" and insert -- poly( --, therefor.

Line 26, delete "ploy(alkenylene" and insert -- poly(alkylene --, therefor.

Line 26, delete "ploy(" and insert -- poly( --, therefor.

Line 51, delete "ploy(alkenylene" and insert -- poly(alkylene --, therefor.

Line 53, delete "alkenylene" and insert -- alkylene --, therefor.

Line 56, delete "ploy(alkenylene" and insert -- poly(alkylene --, therefor.

Line 64, delete "alkenylene" and insert -- alkylene --, therefor.

Line 67, delete "alkenylene" and insert -- alkylene --, therefor.

<u>Column 7,</u>
Line 1, delete "alkenylene" and insert -- alkylene --, therefor.

Line 4, delete "ploy(alkenylene" and insert -- poly(alkylene --, therefor.

Line 5, delete "ploy(" and insert -- poly( --, therefor.

UNITED STATES PATENT AND TRADEMARK OFFICE
CERTIFICATE OF CORRECTION

PATENT NO. : 7,342,047 B2
APPLICATION NO. : 10/792238
DATED : March 11, 2008
INVENTOR(S) : Kevin M. Lewandowski It is certified that error appears in the above-identified patent and that said Letters Patent is hereby corrected as shown below:

Column 7,
Line 6, delete first occurrence "ploy(" and insert -- poly( --, therefor.

Line 6, delete second occurrence "ploy(" and insert -- poly( --, therefor.

Line 17, delete "obligers" and insert -- oligomers --, therefor.

Line 19, delete "pulverizable" and insert -- polymerizable --, therefor.

Line 24, delete "pulverizable" and insert -- polymerizable --, therefor.

Line 29, delete "pulverizable" and insert -- polymerizable --, therefor.

Line 49, delete "(ethynloxy)" and insert -- (ethynyloxy) --, therefor.

Column 8,
Line 7, delete "pulverizable" and insert -- polymerizable --, therefor.

Line 8, delete "obligers" and insert -- oligomers --, therefor.

Line 25, delete "pulverizable" and insert -- polymerizable --, therefor.

Column 9,
Line 15, delete "alkenylene" and insert -- alkylene --, therefor.

Line 17, delete "alkenylene" and insert -- alkylene --, therefor.

Line 18, delete "alkenylene" and insert -- alkylene --, therefor.

Line 23, delete "pulverizable" and insert -- polymerizable --, therefor.

Line 27, delete "pulverizable" and insert -- polymerizable --, therefor.

Line 30, delete "obligers" and insert -- oligomers --, therefor.

UNITED STATES PATENT AND TRADEMARK OFFICE
CERTIFICATE OF CORRECTION

PATENT NO.        : 7,342,047 B2
APPLICATION NO.   : 10/792238
DATED             : March 11, 2008
INVENTOR(S)       : Kevin M. Lewandowski It is certified that error appears in the above-identified patent and that said Letters Patent is hereby corrected as shown below:

Column 9,
Lines 31-32, delete "pulverizable" and insert -- polymerizable --, therefor.

Line 38, delete "pulverizable" and insert -- polymerizable --, therefor.

Line 42, delete "pulverizable," and insert -- polymerizable, --, therefor.

Column 10,
Line 39, delete "isocyanatoclohexyl" and insert -- isocyanatocylohexyl --, therefor.

Line 50, delete "epoxypropoxyophenyl]}" and insert -- epoxypropoxy)phenyl]} --, therefor.

Column 11,
Line 3, delete "pulverizable" and insert -- polymerizable --, therefor.

Line 21, delete "obligers" and insert -- oligomers --, therefor.

Line 44, delete "pulverizable" and insert -- polymerizable --, therefor.

Line 47, delete "ploy(alkenylene" and insert -- poly(alkylene --, therefor.

Lines 59-60, delete "hydroxybutly" and insert -- hydroxybutyl --, therefor.

Column 12,
Line 3, delete "obligers" and insert -- oligomers --, therefor.

Line 11, delete "pulverizable" and insert -- polymerizable --, therefor.

Line 12, delete "pulverizable" and insert -- polymerizable --, therefor.

Line 16, delete "obligers" and insert -- oligomers --, therefor.

Line 42, delete "(IRGACURE 19)," and insert -- "(IRGACURE 819), --, therefor.

UNITED STATES PATENT AND TRADEMARK OFFICE
CERTIFICATE OF CORRECTION

PATENT NO.        : 7,342,047 B2
APPLICATION NO.   : 10/792238
DATED             : March 11, 2008
INVENTOR(S)       : Kevin M. Lewandowski It is certified that error appears in the above-identified patent and that said Letters Patent is hereby corrected as shown below:

Column 13,
Line 25, delete "obligers" and insert -- oligomers --, therefor.

Line 32 and 50, delete "ploy(alkenylene" and insert -- poly(alkylene --, therefor.

Line 50, delete in first occurrence "obligers" and insert -- oligomers --, therefor.

Line 50, delete in second occurrence "obligers" and insert -- oligomers --, therefor.

Line 52, delete "obligers" and insert -- oligomers --, therefor.

Line 54, delete "obligers" and insert -- oligomers --, therefor.

Line 55, delete "pulverizable" and insert -- polymerizable --, therefor.

Line 56, delete "obligers" and insert -- oligomers --, therefor.

Line 61, delete "obligers," and insert -- oligomers, --, therefor.

Line 63, delete "obligers" and insert -- oligomers --, therefor.

Line 65, delete "obligers" and insert -- oligomers --, therefor.

Column 14,
Line 3, delete "obligers" and insert -- oligomers --, therefor.

Line 6, delete "300," and insert -- 300), --, therefor.

Line 8, delete "obligers" and insert -- oligomers --, therefor.

Line 13, delete "obligers" and insert -- oligomers --, therefor.

Line 21, delete "pulverizable" and insert -- polymerizable --, therefor.

UNITED STATES PATENT AND TRADEMARK OFFICE
CERTIFICATE OF CORRECTION

PATENT NO. : 7,342,047 B2
APPLICATION NO. : 10/792238
DATED : March 11, 2008
INVENTOR(S) : Kevin M. Lewandowski It is certified that error appears in the above-identified patent and that said Letters Patent is hereby corrected as shown below:

Column 14,
Line 25, delete "ploy(alkenylene" and insert -- poly(alkylene --, therefor.

Line 26, delete "ploy(" and insert -- poly( --, therefor.

Line 27, delete "ploy(alkenylene" and insert -- poly(alkylene --, therefor.

Line 27, delete "ploy(" and insert -- poly( --, therefor.

Line 51, delete "ploy(alkenylene" and insert -- poly(alkylene --, therefor.

Line 53, delete "alkenylene" and insert -- alkylene --, therefor.

Line 56, delete "ploy(alkenylene" and insert -- poly(alkylene --, therefor.

Line 64, delete "alkenylene" and insert -- alkylene --, therefor.

Lines 66-67, delete "alkenylene" and insert -- alkylene --, therefor.

Column 15,
Line 1, delete "alkenylene" and insert -- alkylene --, therefor.

Line 3, delete "ploy(alkenylene" and insert -- poly(alkylene --, therefor.

Line 4, delete "ploy(" and insert -- poly( --, therefor.

Line 5, delete first occurrence "ploy(" and insert -- poly( --, therefor.

Line 5, delete second occurrence "ploy(" and insert -- poly( --, therefor.

Line 14, delete "pulverizable" and insert -- polymerizable --, therefor.

Line 16, delete "pulverizable" and insert -- polymerizable --, therefor.

Line 17, delete "ploy(alkenylene" and insert -- poly(alkylene --, therefor.

Line 21, delete "obligers" and insert -- oligomers --, therefor.

UNITED STATES PATENT AND TRADEMARK OFFICE
CERTIFICATE OF CORRECTION

PATENT NO. : 7,342,047 B2
APPLICATION NO. : 10/792238
DATED : March 11, 2008
INVENTOR(S) : Kevin M. Lewandowski It is certified that error appears in the above-identified patent and that said Letters Patent is hereby corrected as shown below:

Column 16,
Line 8, delete "pulverizable" and insert -- polymerizable --, therefor.

Line 25, delete "ploy(alkenylene" and insert -- poly(alkylene --, therefor.

Lines 30-31, delete "pulverizable" and insert -- polymerizable --, therefor.

Line 53, delete "nistatin," and insert -- nystatin, --, therefor.

Line 59, delete "prilocaline," and insert -- prilocaine, --, therefor.

Column 19,
Line 60, delete "ploy(" and insert -- poly( --, therefor.

Column 22,
Line 49, delete "methoxypolyetliylene" and insert -- methoxypolyethylene --, therefor.

Line 51, delete "et al)." and insert -- et al.). --, therefor.

Column 27,
Line 30, in claim 21, delete "obligers" and insert -- oligomers --, therefor.

Signed and Sealed this

Ninth Day of December, 2008

JON W. DUDAS
*Director of the United States Patent and Trademark Office*